United States Patent [19]

Cale, Jr. et al.

[11] Patent Number: 5,063,228
[45] Date of Patent: Nov. 5, 1991

[54] 4-(SUBSTITUTEDAMINOETHYL)-3,4-DIHYDRO-2-ALKYLPYRIMIDO08 1,6-A09 BENZIMIDAZOL-1(2H)-ONES AS ANTIARRHYTHMIC AGENTS

[75] Inventors: Albert D. Cale, Jr., Mechanicsville; Thomas W. Gero, Richmond, both of Va.

[73] Assignee: A. H. Robbins Company, Incorporated, Richmond, Va.

[21] Appl. No.: 531,137

[22] Filed: May 31, 1990

[51] Int. Cl.$^5$ ............... A61K 31/495; A61K 31/505; C07D 487/06
[52] U.S. Cl. .................................. 574/253; 514/267; 544/230; 544/253
[58] Field of Search ............... 544/230, 250; 514/253, 514/267

[56] References Cited

U.S. PATENT DOCUMENTS 4,041,163  8/1977  Bindra et al. .................. 544/250
4,109,091  8/1978  Denzel et al. .................. 544/250

OTHER PUBLICATIONS

Carl, CA 63-11504b(19.
A. H. Robbins Co., Inc. Inc. CA 65-20136h (1966).

Primary Examiner—Cecilia Shen
Attorney, Agent, or Firm—Donald E. Gillespie

[57] ABSTRACT

Novel compounds of the formula:

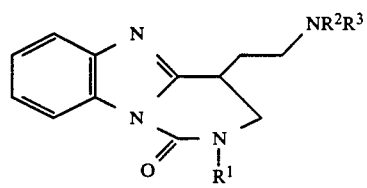

Where $R^1$ is loweralkyl and $R^2$ and $R^3$ are independently H, loweralkyl, aryl, or —$NR^2R^3$ forms a heterocyclic group such as imidazole, morpholine, piperidine, or piperazine were found to exhibit cardiac arrhythmia correcting properties.

15 Claims, No Drawings

4-(SUBSTITUTEDAMINOETHYL)-3,4-DIHYDRO-2-ALKYLPYRIMIDO[1,6-A] BENZIMIDAZOL-1(2H)-ONES AS ANTIARRHYTHMIC AGENTS

BACKGROUND OF THE INVENTION

1. Field of Invention

This invention relates to novel 4-(substitutedaminoethyl)-3,4-dihydro-2-alkylpyrimido[1,6-a]benzimidazol-1(2H)-ones which are useful in treating cardiac arrhythmias in warm-blooded animals.

2. Information Disclosure Statement

A search of the chemical and patent literature did not disclose any of the compounds of this invention.

SUMMARY OF THE INVENTION

The compounds of this invention are represented by Formula I below:

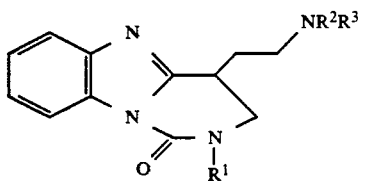

Formula I

Under this formula, $R^1$ is loweralkyl and $R^2$ and $R^3$ are independently selected from H, loweralkyl or aryl or $-NR^2R^3$ forms a heterocyclic group such as morpholine, imidazole,

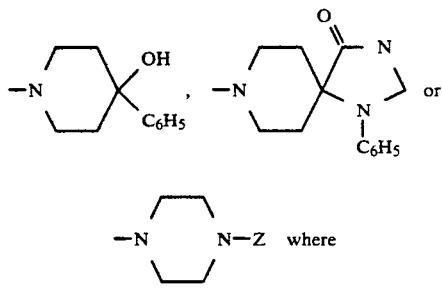

Z is loweralkyl, aryl, 2-pyridinyl or 2-pyrimidinyl. Formula I also encompasses the optical isomers and the pharmaceutically acceptable salts thereof.

The term loweralkyl refers to a straight or branched hydrocarbon radical of from 1 to 6 carbons such as methyl, ethyl, propyl, 2-propyl, butyl, t-butyl, pentyl or hexyl and the like. Aryl refers to a phenyl group or a phenyl group substituted by 1 or 2 substituents selected from the group consisting of halogen, hydroxy, loweralkyloxy, loweralkylcarbonyl and the like. The term halogen refers to fluorine, chlorine, bromine or iodine.

The term optical isomers includes enantiomers, diastereomers and geometric isomers wherever such are possible.

The term pharmaceutically acceptable salts includes the acid addition salts, solvates, and quaternary salts. The pharmaceutically acceptable acid addition salts includes those formed from strong acids such as hydrochloric acid, hydrobromic acid, sulfuric acid, phosphoric acid, and methanesulfonic acid and from weaker acids such as acetic acid, fumaric acid, oxalic acid, cyclohexylsulfamic acid, maleic acid, citric acid and the like. Solvates include water and/or other solvents utilized in the preparation and purification of Formula I compounds. Quaternary salts include those formed by addition of a $C_1-C_6$ alkyl halide such as methyl iodide or ethyl iodide or a benzylic halide such as benzyl bromide.

Antiarrhythmic activity is determined using the coronary occlusion-induced arrhythmia procedure in the conscious dog.

DETAILED DESCRIPTION OF THE INVENTION

The novel Formula I compounds are prepared from intermediate 4-(2-chloroethyl)-3,4-dihydro-2-loweralkylpyrimido[1,6-a]benzimidazol-1-(2H)-ones (2) which are prepared from 2-(1-loweralkyl-3-pyrrolidinyl)-1H-benzimidazoles (1) according to the following reaction sequences:

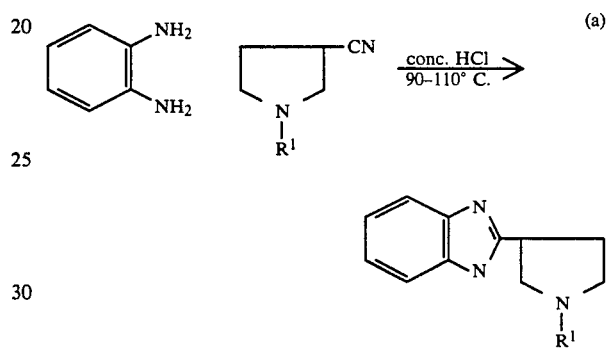

The 3-cyano-1-loweralkylpyrrolidine is added to concentrated hydrochloric acid. After the temperature of the exothermic reaction begins to subside the mixture is heated, preferably to 110° C. for 4 hours. The mixture is cooled to 60° C. and treated with a mixture of 1,2-phenylenediamine in concentrated hydrochloric acid. The reaction mixture is then stirred at reflux for about 20 h. The mixture is cooled and basified carefully with concentrated ammonium hydroxide and the crude solid product collected. The product is purified by procedures known to those skilled in the art.

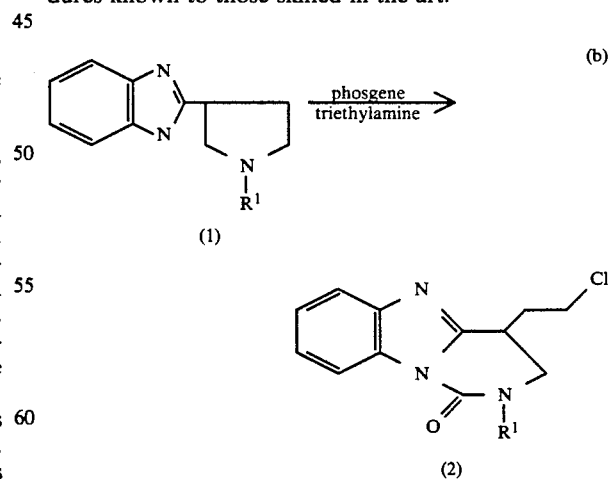

Reaction of the 2-(1-loweralkyl-3-pyrrolidinyl)-1H-benzimidazole (1) with phosgene in an aprotic solvent such as methylene chloride with an acid acceptor such as triethylamine yields the intermediate 4-(2-chloroethyl)-3,4-dihydro-2-loweralkylpyrimido[1,6-a]benzimidazol- 1(2H)-ones (2). This ring-opening rearrangement reaction was disclosed in our commonly owned U.S. Pat. Nos. 3,337,580 and 3,192,230 and 3,192,221.

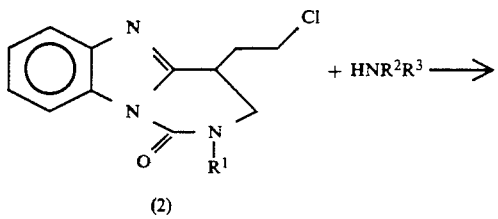

(2)

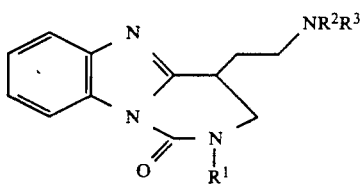

Formula I

The Formula I compounds are obtained by reacting the intermediate (2) with the proper amine $HNR^2R^3$ in a suitable solvent such as toluene or with a large excess of $HNR^2R^3$ which serves both as solvent and reactant.

The optical isomers can be separated by standard laboratory procedures known to those skilled in the art.

The foregoing methods of preparation of compounds of Formula I and intermediates thereto are broadly described and the reactions may not be applicable as described to each compound included within the scope of this invention.

Other synthetic procedures for the preparation of compounds of this invention will be apparent to those skilled in the art and this disclosure should not be construed as limiting in any way.

Without further elaboration, it is believed that one skilled in the art will be able to carry out this invention without undue experimentation. The following preparations and examples are therefore to be construed as illustrative and not limiting to this disclosure in any way. The various reagents used in the following preparations and examples are either commercially available or readily synthesized by procedures given in the chemical and patent literature.

PREPARATION 1

2-(1-Methyl-3-pyrrolidinyl)-1H-benzimidazole.

To 240 g of concentrated hydrochloric acid was added 43.2 g (0.39 mol) of 3-cyano-1-methylpyrrolidine (the temperature rose to 90° C.). After the temperature began to fall the solution was heated to 110° C. for 4 h. The solution was cooled to 60° C. and 42 g (0.39 mol) of 1,2-diaminobenzene in 250 mL of 1N hydrochloric acid was added. The solution was heated to reflux for 20 h. The cooled solution was made basic with concentrated $NH_4OH$ and the resulting crystals were collected by filtration. The product was chromatographed on a 7.5×36 cm silica column eluting with 1 gallon of 10% $NH_4OH$-90% ethanol. The eluent was collected in 500-mL portions. The first 6 fractions were discarded and fractions 7-14 were collected and concentrated. The residue was recrystallized from ethyl acetate. Yield: 18 g (23%). A 5-g sample was recrystallized three times from ethyl acetate. Yield: 1.6 g, mp 189°-193° C.

| Analysis: | |
|---|---|
| Calculated for $C_{12}H_{15}N_3$: | C, 71.61; H, 7.51; N, 20.88 |
| Found: | C, 71.13; H, 7.47; N, 20.64 |

PREPARATION 2

4-(2-Chloroethyl)-3,4-dihydro-2-methyl-pyrimido[1,6-a]benzimidazol-1(2H)-one.

A solution of 4 g (0.02 mol) of 2-(1-methyl-3-pyrrolidinyl)-1H-benzimidazole in 100 mL of $CH_2Cl_2$ was added dropwise to a solution of 12.5 (0.025 mol) of 20% phosgene/toluene in 30 mL of $CH_2Cl_2$. The solution was stirred for 2 h, and 10 g (0.1 mol) of triethylamine was added dropwise. Stirring was continued for 2 h and the solution was extracted with dilute NaOH. The organic layer was dried ($Na_2SO_4$) and concentrated. The residue was crystallized twice from isopropyl ether. Yield 1.5 g (28%), mp 88°-91° C.

| Analysis: | |
|---|---|
| Calculated for $C_{13}H_{14}N_3OCl$: | C, 59.21; H, 5.35; N, 15.93 |
| Found: | C, 59.18; H, 5.38; N, 15.89 |

PREPARATION 3

Following the procedure of Preparation 1 and substituting for 3-cyano-1-methylpyrrolidine with the following:

a. 3-cyano-1-ethylpyrrolidine
   b. 3-cyano-1-(1-methylethyl)pyrrolidine
   c. 3-cyano-1-propylpyrrolidine
   d. 3-cyano-1-butylpyrrolidine
there are obtained respectively:
   a. 2-(1-ethyl-3-pyrrolidinyl)-1H-benzimidazole
   b. 2-[1-(1-methylethyl)-3-pyrrolidinyl]-1H-benzimidazole
   c. 2-(1-propyl-3-pyrrolidinyl)-1H-benzimidazole
   d. 2-[1-butyl-3-pyrrolidinyl)-1H-benzimidazole.

PREPARATION 4

Following the procedure of Preparation 2 and substituting the following for 2-(1-methyl-3-pyrrolidinyl)-1H-benzimidazole:

a. 2-(1-ethyl-3-pyrrolidinyl)-1H-benzimidazole
   b. 2-[1-(1-methylethyl)-3-pyrrolidinyl]-1H-benzimidazole
   c. 2-(1-propyl-3-pyrrolidinyl)-1H-benzimidazole
   d. 2-[1-butyl-3-pyrrolidinyl)-1H-benzimidazole
there are obtained respectively:
   a. 4-(2-chloroethyl)-3,4-dihydro-2-ethylpyrimido[1,6-a]benzimidazol-1(2H)-one
   b. 4-(2-chloroethyl)-3,4-dihydro-2-(1-methylethyl)-pyrimido[1,6-a]benzimidazol-1(2H)-one
   c. 4-(2-chloroethyl)-3,4-dihydro-2-propyl-pyrimido[1,6-a]benzimidazol-1(2H)-one
   d. 4-(2-chloroethyl)-3,4-dihydro-2-butyl-pyrimido[1,6-a]-benzimidazol-1(2H)-one.

EXAMPLE 1

4-[2-(Dimethylamino)ethyl]-3,4-dihydro-2-methyl-pyrimido[1,6-a]benzimidazol-1(2H)-one (Z)-2-Butenedioate (1:1) Hemihydrate.

To 25 mL of dimethylamine was added 5 g (0.019 mol) of 4-(2-chloroethyl)-3,4-dihydro-2-methyl-pyrimido[1,6-a]benzimidazol-1(2H)-one. The mixture was sealed in a glass flask and stirred for 48 h. The flask was opened and the excess dimethylamine was allowed to evaporate. The residue was partitioned between $CH_2Cl_2$ and dilute NaOH. The organic phase was dried ($Na_2SO_4$) and concentrated. The residue was dissolved in 60 mL of isopropyl alcohol and treated with 2.2 g (0.019 mol) of maleic acid. The resulting crystals were recrystallized from isopropyl alcohol containing a few drops of water. Yield 4.6 g (61%), mp 138°–145° C.

| Analysis: | |
|---|---|
| Calculated for $C_{38}H_{49}N_8O_{11}$: | C, 57.39; H, 6.37; N, 14.09 |
| Found: | C, 57.69; H, 6.24; N, 13.94 |

EXAMPLE 2

3,4-Dihydro-2-methyl-4-[2-(4-morpholinyl)ethyl]-pyrimido[1.6-a]benzimidazol-1(2H)-one.

To 20 mL of morpholine was added 3.5 g (0.0133 mol) of 4-(2-chloroethyl)-3,4-dihydro-2-methylpyrimido[1,6-a]benzimidazol-1(2H)-one. The reaction mixture was heated in 60° C. for 24 hrs. The excess morpholine was removed by rotary evaporation and finally by high vacuum (0.5 mm Hg ~60° C.). The residue was dissolved in ~100 mL of $CH_2Cl_2$ washed with 3×50 ml of 1N NaOH, dried over $Na_2SO_4$, filtered, and concentrated by rotary evaporation. The residue was crystallized from isopropyl ether to give 2.7 g (65%) of analytically pure crystals, mp 111°–12° C.

| Analysis: | |
|---|---|
| Calculated for $C_{17}H_{22}N_4O_2$: | C, 64.95; H, 7.05; N, 17.82 |
| Found: | C, 64.93; H, 7.10; N, 17.72 |

EXAMPLE 3

3,4-Dihydro-2-methyl-4-[2-(methylphenylamino)ethyl]pyrimido[1.6-a]benzimidazol-1(2H)-one.

To 15 mL of N-methylaniline was added 3.5 g (0.0133 mol) of 4-(2-chloroethyl)-3,4-dihydro-2-methyl-pyrimido[1,6-a]benzimidazol-1(2H)-one. The reaction mixture was heated to 90° C. (oil bath) for 2 days, and the excess N-methylaniline removed in vacuo at 80° C., 0.5 mm Hg. The residue was dissolved in 100 mL of $CH_2Cl_2$, washed with 2×100 mL of 1N NaOH, dried over $Na_2SO_4$, filtered, and concentrated by rotary evaporation. The residue was subjected to high vacuum (0.5 mm, Hg) at 85° C. for 2 hr, and then crystallized from iso-octane/toluene to give 2.3 g (52%) of analytically pure crystals, mp 130°–31° C.

| Analysis: | |
|---|---|
| Calculated for $C_{20}H_{22}N_4O$: | C, 71.83; H, 6.63; N, 16.75 |
| Found: | C, 72.07; H, 6.69; N, 16.65 |

EXAMPLE 4

3,4-Dihydro-2-methyl-4-[2-(methyl-1-piperazinyl)ethyl]pyrimido[1,6-a]benzimidazol-1(2H)-one.

To 18 mL of N-methylpiperazine was added 3.5 g (0.0133 mol) of 4-(2-chloroethyl)-3,4-dihydro-2-methyl-pyrimido[1,6-a]benzimidazol-1(2H)-one. The reaction mixture was heated 60° C. (oil bath) for 24 hr and the excess N-methylpiperazine removed at ~60° C., 0.5 mm Hg. The residue was dissolved in 100 mL of $CH_2Cl_2$, washed with 2×50 mL of 1N NaOH, dried over $Na_2SO_4$, filtered, and concentrated by rotary evaporation. The residue was dissolved in toluene, treated with charcoal, filtered, and concentrated by rotary evaporation. The residue was crystallized from iso-octane/toluene to give 2.4 g (55%) of analytically pure crystals, mp 110°–12° C.

| Analysis: | |
|---|---|
| Calculated for $C_{18}H_{25}N_5O$: | C, 66.03; H, 7.70; N, 21.39 |
| Found: | C, 66.01; H, 7.76; N, 21.07 |

EXAMPLE 5

3,4-Dihydro-4-[2-(4-hydroxy-4-phenyl-1-piperidinyl)ethyl]-2-methylpyrimido[1.6-a]benzimidazol1(2H)-one (E)-2-butenedioate (2:3).

To a solution of 4.0 g (0.015 mol) of 4-(2-chloroethyl)-3,4-dihydro-2-methylpyrimido[1,6-a]benzimidazol-1(2H)-one dissolved in 20 mL of toluene was added 4.0 g (0.023 mol) of 4-hydroxy-4-phenylpiperidine and 4.0 g (0.04 mol) of triethylamine. The reaction mixture was heated to reflux for 24 hr and the solvent removed by rotary evaporation. The residue was dissolved in 100 mL of $CH_2Cl_2$, washed with 2×50 mL of 1N NaOH, dried over $Na_2SO_4$, filtered, and concentrated by rotary evaporation. The residue was subjected to preparative high pressure liquid chromatography (preparative HPLC) using ethanol as the eluent and silica gel as the stationary phase. The residue was treated with fumaric acid in isopropyl alcohol to give 3.2 g (36.5%) of analytically pure crystals, mp 214°–17° C.

| Analysis: | |
|---|---|
| Calculated for $C_{39}H_{35}N_4O_6$: | C, 62.17; H, 6.09; N, 9.67 |
| Found: | C, 62.20; H, 6.07; N. 9.61 |

EXAMPLE 6

3,4-Dihydro-2-methyl-4-[2-(4-phenyl-1-piperazinyl)ethyl]pyrimido[1,6-a]benzimidazol-1(2H)-one.

To 4.0 g (0.015 mol) of 4-(2-chloroethyl)-3,4-dihydro-2-methylpyrimido[1,6-a]benzimidazol-1(2H)-one in 35 mL of toluene was added 6.5 g (0.04 mol) of N-phenylpiperazine. The reaction mixture was heated to reflux for 2 days. The entire reaction mixture was washed with 3×50 mL of 1N NaOH, dried over $Na_2SO_4$, filtered, and concentrated by rotary evaporation. The residue was subjected to preparative HPLC using acetone as the eluent and silica gel as the stationary phase. Like fractions were combined, concentrated and the residue crystallized from isopropyl alcohol to give 3.7 g (64%) of analytically pure, crystalline material, mp 143.5°–145.5° C.

| Analysis: | |
|---|---|
| Calculated for $C_{23}H_{27}N_5O$: | C, 70.93; H, 6.99; N, 17.98 |
| Found: | C, 70.77; H, 7.02; N, 17.81 |

EXAMPLE 7

3,4-Dihydro-2-methyl-4-[2-[4-(2-pyridinyl)-1-piperazinyl]ethyl]-pyrimido[1,6-a]benzimidazol-1(2H)-one.

To 50 mL of toluene was added 5.0 g (0.019 mol) of 4-(2-chloroethyl)-3,4-dihydro-2-methylpyrimido[1,6-a]benzimidazol-1(2H)-one, 6.19 g (0.038 mol) of 1-(2-pyridyl)piperazine, and 3.8 g (0.038 mol) of triethylamine. The reaction mixture was heated to reflux for 24 hours. The reaction mixture was washed with 2×50 mL of NaOH, dried over $Na_2SO_4$, filtered and concentrated by rotary evaporation. The residue was crystallized from isopropyl alcohol to afford 5.5 g (75%) of analytically pure crystals, mp 158°–59° C.

| Analysis: | |
|---|---|
| Calculated for $C_{22}H_{26}N_6O$: | C, 67.67; H, 6.71; N, 21.52 |
| Found: | C, 67.69; H, 6.75; N, 21.50 |

EXAMPLE 8

3,4-Dihydro-2-methyl-4-[2-[4-(2-pyrimidinyl)-1-piperazinyl]ethyl]-pyrimido[1,6-a]benzimidazol-1(2H)-one.

To 60 mL of toluene was added 4.0 g (0.0152 mol) of 4-(2-chloroethyl)-3,4-dihydro-2-methylpyrimido[1,6-a]benzimidazol-1(2H)-one, 6.0 g (0.033 mol) of 1-(2-pyrimidyl)piperazine, and 4.0 g (0.04 mol) of triethylamine. The reaction mixture was heated at reflux for 2 days and subsequently washed with 2×50 mL of 1N NaOH, dried over $Na_2SO_4$, filtered, and concentrated by rotary evaporation. Crystallization from ethyl acetate afforded 4.0 g, 67% of analytically pure crystals, mp 161°–62° C.

| Analysis: | |
|---|---|
| Calculated for $C_{21}H_{25}N_7O$: | C, 64.43; H, 6.44; N, 25.05 |
| Found: | C, 64.35; H, 6.40; N, 24.90 |

EXAMPLE 9

Following the procedure of Example 1 and substituting for 4-(2-chloroethyl)-3,4-dihydro-2-methyl-pyrimido[1,6-a]benzimidazol-1(2H)-one the following:
  a. 4-(2-chloroethyl)-3,4-dihydro-2-ethylpyrimido[1,6-a]benzimidazol-1(2H)-one
  b. 4-(2-chloroethyl)-3,4-dihydro-2-(1-methylethyl)-pyrimido[1,6-a]benzimidazol-1(2H)one
  c. 4-(2-chloroethyl)-3,4-dihydro-2-propyl-pyrimido[1,6-a]benzimidazol-1(2H)-one
  d. 4-(2-chloroethyl)-3,4-dihydro-2-butyl-pyrimido[1,6-a]benzimidazol-1(2H)-one
there are obtained respectively:
  a. 4-[2-(dimethylamino)ethyl]-3,4-dihydro-2-ethyl-pyrimido[1,6-a]benzimidazol-1(2H)-one
  b. 4-[2-(dimethylamino)ethyl]3,4-dihydro-2-(1-methylethyl)pyrimido[1,6-a]benzimidazol-1(2H)-one
  c. 4-[2-(dimethylamino)ethyl]3,4-dihydro-2-propyl-pyrimido[1,6-a]benzimidazol-1(2H)one
  d. 4-[2-(dimethylamino)ethyl]-3,4-dihydro-2-butyl-pyrimido[1,6-a]benzimidazol-1(2H)one.

EXAMPLE 10

Following the procedure of Example 2 and substituting for 4-(2-chloroethyl)-3,4-dihydro-2-methyl-pyrimido[1,6-a]benzimidazol-1(2H)-one the following:
  a. 4-(2-chloroethyl)-3,4-dihydro-2-ethylpyrimido[1,6-a]benzimidazol-1(2H)-one
  b. 4-(2-chloroethyl)-3,4-dihydro-2-(1-methylethyl)-pyrimido[1,6-a]benzimidazol-1(2H)one
  c. 4-(2-chloroethyl)-3,4-dihydro-2-propyl-pyrimido[1,6-a]benzimidazol-1(2H)-one
  d. 4-(2-chloroethyl)-3,4-dihydro-2-butyl-pyrimido[1,6-a]benzimidazol-1(2H)-one
there are obtained respectively:
  a. 3,4-dihydro-2-ethyl-4-[2-(4-morpholinyl)ethyl]-pyrimido[1,6-a]benzimidazol-1(2H)-one
  b. 3,4-dihydro-2-(1-methylethyl)-4-[2-(4-morpholinyl)ethyl]pyrimido[1,6-a]benzimidazol-1(2H)-one
  c. 3,4-dihydro-4-[2-(4-morpholinyl)ethyl]-2-propyl-pyrimido[1,6-a]benzimidazol-1(2H)-one
  d. 2-butyl-3,4-dihydro-4-[2-(4-morpholinyl)ethyl]-pyrimido[1,6-a]benzimidazol-1(2H)-one.

EXAMPLE 11

Following the procedure of Example 3 and substituting for 4-(2-chloroethyl)-3,4-dihydro-2-methyl-pyrimido[1,6-a]benzimidazol-1(2H)-one the following:
  a. 4-(2-chloroethyl)-3,4-dihydro-2-ethylpyrimido[1,6-a]benzimidazol-1(2H)-one
  b. 4-(2-chloroethyl)-3,4-dihydro-2-(1-methylethyl)-pyrimido[1,6-a]benzimidazol-1(2H)-one
  c. 4-(2-chloroethyl)-3,4-dihydro-2-propyl-pyrimido[1,6-a]benzimidazol-1(2H)-one
  d. 4-(2-chloroethyl)-3,4-dihydro-2-butyl-pyrimido[1,6-a]benzimidazol-1(2H)-one
there are obtained respectively:
  a. 3,4-dihydro-2-ethyl-4-[2-(methylphenylamino)ethyl]pyrimido[1,6-a]benzimidazol-1(2H)-one
  b. 3,4-dihydro-2-(1-methylethyl)-4-[2-(methylphenylamino)ethyl]-pyrimido[1,6-a]benzimidazol-1(2H)-one
  c. 3,4-dihydro-4-[2-(methylphenylamino)ethyl]-2-propylpyrido[1,6-a]benzimidazol-1(2H)-one
  d. 2-butyl-3,4-dihydro-4-[2-(methylphenylamino)ethyl]pyrido[1,6-a]benzimidazole.

EXAMPLE 12

Following the procedure of Example 4 and substituting for 4-(2-chloroethyl)-3,4-dihydro-2-methyl-pyrimido[1,6-a]benzimidazol-1(2H)-one the following:
  a. 4-(2-chloroethyl)-3,4-dihydro-2-ethylpyrimido[1,6-a]benzimidazol-1(2H)-one
  b. 4-(2-chloroethyl)-3,4-dihydro-2-(1-methylethyl)-pyrimido[1,6-a]benzimidazol-1(2H)-one
  c. 4-(2-chloroethyl)-3,4-dihydro-2-propyl-pyrimido[1,6-a]benzimidazol-1(2H)-one
  d. 4-(2-chloroethyl)-3,4-dihydro-2-butyl-pyrimido[1,6-a]benzimidazol-1(2H)-one.
there are obtained respectively:
  a. 3,4-dihydro-2-ethyl-4-[2-(4-methyl-1-piperazinyl)ethyl]pyrimido[1,6-a]benzimidazol-1(2H)-one
  b. 3,4-dihydro-2-(1-methylethyl)-4-[2-(4-methyl-1-piperazinyl)-ethyl]pyrimido[1,6-a]benzimidazol-1(2H)-one
  c. 3,4-dihydro-4-[2-(methyl-1-piperazinyl)ethyl]-2-propylpyrimido[1,6-a]benzimidazol-1(2H)-one
  d. 2-butyl-3,4-dihydro-4-[2-(4-methyl-1-piperazinyl)-ethylpyrimido[1,6-a]benzimidazol-1(2H)-one.

EXAMPLE 13

Following the procedure of Example 5 and substituting for 4-(2-chloroethyl)-3,4-dihydro-2-methyl-pyrimido[1,6-a]benzimidazol-1(2H)-one the following:
  a. 4-(2-chloroethyl)-3,4-dihydro-2-ethylpyrimido[1,6-a]benzimidazol-1(2H)-one
  b. 4-(2-chloroethyl)-3,4-dihydro-2-(1-methylethyl)-pyrimido[1,6-a]benzimidazol-1(2H)-one c. 4-(2-chloroethyl)-3,4-dihydro-2-propyl-pyrimido[1,6-a]benzimidazol-1(2H)-one
d. 4-(2-chloroethyl)-3,4-dihydro-2-butyl-pyrimido[1,6-a]benzimidazol-1(2H)-one
there are obtained respectively:
a. 3,4-dihydro-2-ethyl-4-[2-(4-hydroxy-4-phenyl-1-piperidinyl)ethyl]pyrimido[1,6-a]benzimidazol-1(2H)-one
b. 3,4-dihydro-4-[2-(4-hydroxy-4-phenyl-1-piperidinyl)ethyl]-2-(1-methylethyl)pyrimido[1,6-a]benzimidazol-1(2H)-one
c. 3,4-dihydro-4-[2-(4-hydroxy-4-phenyl-1-piperidinyl)ethyl]2-propylpyrimido[1,6-a]benzimidazol-1(2H)-one
d. 2-butyl-3,4-dihydro-4-[2-(4-hydroxy-4-phenyl-1-piperidinyl)ethyl]pyrimido[1,6-a]benzimidazol-1(2H)-one.

EXAMPLE 14

Following the procedure of Example 6 and substituting for 4-(2-chloroethyl)-3,4-dihydro-2-methyl-pyrimido[1,6-a]benzimidazol-1(2H)-one the following:
a. 4-(2-chloroethyl)-3,4-dihydro-2-ethylpyrimido[1,6-a]benzimidazol-1(2H)-one
b. 4-(2-chloroethyl)-3,4-dihydro-2-(1-methylethyl)-pyrimido[1,6-a]benzimidazol-1(2H)-one
c. 4-(2-chloroethyl)-3,4-dihydro-2-propyl-pyrimido[1,6-a]benzimidazol-1(2H)-one
d. 4-(2-chloroethyl)-3,4-dihydro-2-butyl-pyrimido[1,6-a]benzimidazol-1(2H)-one
there are obtained respectively:
a. 3,4-dihydro-2-ethyl-4-[2-(4-phenyl-1-piperazinyl)ethyl]-pyrimido[1,6-a]benzimidazol-1(2H)-one
b. 3,4-dihydro-2-(1-methylethyl)-4-[2-(4-phenyl-1-piperazinyl)ethyl]pyrimido[1,6-a]benzimidazol-1(2H)-one
c. 3,4-dihydro-4-[2-(4-phenyl-1-piperazinyl)ethyl]-2-propylpyrimido[1,6-a]benzimidazol-1(2H)-one
d. 2-butyl-3,4-dihydro-4-[2-(4-phenyl-1-piperazinyl)ethyl]pyrimido[1,6-a]benzimidazol-1(2H)-one.

EXAMPLE 15

Following the procedure of Example 7 and substituting for 4-(2-chloroethyl)-3,4-dihydro-2-methyl-pyrimido[1,6-a]benzimidazol-1(2H)-one the following:
a. 4-(2-chloroethyl)-3,4-dihydro-2-ethylpyrimido[1,6-a]benzimidazol-1(2H)-one
b. 4-(2-chloroethyl)-3,4-dihydro-2-(1-methylethyl)-pyrimido[1,6-a]benzimidazol-1(2H)-one
c. 4-(2-chloroethyl)-3,4-dihydro-2-propyl-pyrimido[1,6-a]benzimidazol-1(2H)-one
d. 4-(2-chloroethyl)-3,4-dihydro-2-butyl-pyrimido[1,6-a]benzimidazol-1(2H)-one
there are obtained respectively:
a. 3,4-dihydro-2-ethyl-4-[2-(4-(2-pyridinyl)-1-piperazinyl)ethyl]-pyrimido[1,6-a]benzimidazol-1(2H)-one
b. 3,4-dihydro-2-(1-methylethyl)-4-[2-(4-(2-pyridinyl)-1-piperazinyl)ethyl]pyrimido[1,6-a]benzimidazol-1(2H)-one
c. 3,4-dihydro-2-propyl-4-[2-[4-(2-pyridinyl)-1-piperazinyl)ethyl]pyrimido[1,6-a]benzimidazol-1(2H)-one
d. 2-butyl-3,4-dihydro-4-[2-(4-(2-pyridinyl)-1-piperazinyl]ethyl]pyrimido[1,6-a]benzimidazol-1(2H)-one.

EXAMPLE 16

Following the procedure of Example 8 and substituting for 4-(2-chloroethyl)-3,4-dihydro-2-methyl-pyrimido[1,6-a]benzimidazol-1(2H)one the following:
a. 4-(2-chloroethyl)-3,4-dihydro-2-ethylpyrimido[1,6-a]benzimidazol-1(2H)-one
b. 4-(2-chloroethyl)-3,4-dihydro-2-(1-methylethyl)-pyrimido[1,6-a]benzimidazol-1(2H)-one
c. 4-(2-chloroethyl)-3,4-dihydro-2-propyl-pyrimido[1,6-a]benzimidazol-1(2H)-one
d. 4-(2-chloroethyl)-3,4-dihydro-2-butyl-pyrimido[1,6-a]benzimidazol-1(2H)-one
there are obtained respectively:
a. 3,4-dihydro-2-ethyl-4-[2-(4-(2-pyrimidinyl))-1-piperazinyl)ethyl]-pyrimido[1,6-a]benzimidazol-1(2H)-one
b. 3,4-dihydro-2-(1-methylethyl)-4-[2-(4-(2-pyrimidinyl)-1-piperazinyl)ethyl]pyrimido[1,6-a]benzimidazol-1(2H)-one
c. 3,4-dihydro-2-propyl-4-[2-[4-(2-pyrimidinyl)-1-piperazinyl)ethyl]pyrimido[1,6-a]benzimidazol-1(2H)-one
d. 2-butyl-3,4-dihydro-4-[2-(4-(2-pyrimidinyl)-1-piperazinyl]ethyl]pyrimido[1,6-a]benzimidazol-1(2H)-one.

EXAMPLE 17

3,4-Dihydro-2-methyl-4-[2-(4-oxo-1-phenyl-1,3,8-triazaspiro[4,5]dec-8-yl)ethyl]pyrimido[1,6-A]benzimidazol-1(2H)-one ethyl acetate (1:1).

A mixture of 4.0 g (0.015 mol) of 4-(2-chloroethyl)-3,4-dihydro-2-methylpyrimido[1,6-a]benzimidazole-1(2H)-one, 3.46 g (0.015 mol) of 1-phenyl-1,3,8-triazaspiro[4,5]-decan-4-one, 9 g of NaHCO$_3$, 0.5 g of KI, and 35 mL of DMF was heated on a steam cone for 24 h. The reaction mixture was poured into 500 mL of H$_2$O and extracted with 3×100 mL of CH$_2$Cl$_2$. The combined organic extracts were washed with 2×100 mL of H$_2$O, dried (NaSO$_4$), filtered and concentrated by rotary evaporation. The residue was purified by preparative HPLC using acetone and the eluent and silica gel as the stationary phase. Like fractions were combined and concentrated by rotary evaporation to a glass which crystallized upon treatment with ethyl acetate to give 4.3 g (52%) of analytically pure material, mp 173°–75° C.

| Analysis: | |
|---|---|
| Calc. for $C_{20}H_{30}N_6O_2 \cdot C_4H_8O_2$: | C, 65.91; H, 7.01; N, 15.37 |
| Found: | C, 65.58; H, 7.00; N, 15.72 |

EXAMPLE 18

3,4-Dihydro-4-[2-[4-(2-methoxyphenyl)-1-piperazinyl]ethyl]-2-methylpyrimido[1,6-a]benzimidazol-1(2H)-one (E)-2-butendioate (2:3).

A mixture of 4.0 g (0.015 mol) of 4-(2-chloroethyl)-3,4-dihydro-2-methylpyrimido[1,6-a]benzimidazole-1(2H)-one, 2.93 g (0.015 mol) of 1-(2-methoxyphenyl)-piperazine, 9 g of NaHCO$_3$, 0.5 g of KI, and 30 mL of DMF was heated on a steam cone for 18 h. The reaction mixture was poured into 400 mL of H$_2$O and extracted with 2×100 mL CH$_2$Cl$_2$. The combined organic layers were dried (Na$_2$SO$_4$), filtered and concentrated by rotary evaporation. The resulting oil was purified by preparative HPLC eluting with acetone and using silica gel as the stationary phase. Like fractions were combined and concentrated by rotary evaporation to an oil. The oil was treated with fumaric acid in 2-propanol to give 3.7 g (42%) of the salt, mp 100°-108° C. dec.

| Analysis: | |
|---|---|
| Calc. for $C_{24}H_{29}N_5O_2 \cdot 1.5C_4H_4O_4$: | C, 60.70; H, 5.44; N, 11.80 |
| Found: | C, 60.71; H, 6.32; N, 11.44 |

EXAMPLE 19

3,4-Dihydro-2-methyl-4-[2-(1H-imidazol-1-yl)ethyl]-pyrimido[1,6-A]benzimidazol-1(2H)-one ethanedioate (2:3).

A solution of 2.4 g (0.035 mol) of imidazole, 3.0 g (0.011 mol) of 4-(2-chloroethyl)-3,4-dihydro-2-methyl-pyrimido[1,6-a]benzimidazol-1(2H)-one and 3.0 g (0.03 mol) of triethylamine in 80 mL of EtOH was heated to reflux. After 24 hr 1.6 g of imidazole was added followed by an additional 1.6 g 24 hr later. Another 1.0 g of imidazole was added and reflux continued for 3 days. The solvent was removed by rotary evaporation. The residue was taken up in $CH_2Cl_2$, washed with 100 mL of 1N NaOH, 3×100 mL of $H_2O$, dried over $Na_2SO_4$, filtered and concentrated by rotary evaporation. The residue was treated with oxalic acid in 2-propanol to give 0.5 g (11%) of crystalline product, mp 148°-49° C.

| Analysis: | |
|---|---|
| Calc. for $C_{16}H_{17}N_5O \cdot 1.5C_2H_2O_4$: | C, 53.02; H, 4.68; N, 16.27 |
| Found: | C, 52.56; H, 4.64; N, 15.99 |

EXAMPLE 20

4-[2-[Bis(4-fluorophenyl)methyl-1-piperidinyl]ethyl]-3,4-dihydro-2-methylpyrimido[1,6-a]benzimidazol-1(2H)-one.

To 4.0 g (0.015 mol) of 4-(2-chloroethyl)-3,4-dihydro-2-methylpyrimido[1,6-a]benzimidazol-1(2H)-one in 20 mL of toluene was added 5.0 g (0.0175 mol) of 4-[bis(4-fluorophenyl)methyl]piperidine and 5.0 g (0.05 mol) of triethylamine and the reaction mixture heated to reflux for 24 hr. The reaction mixture was washed with 3×50 mL of 1N NaOH, dried over $Na_2SO_4$, filtered, and concentrated by rotary evaporation. The residue was subjected to preparative HPLC using ethanol as the eluent and silica gel as the stationary phase. Like fractions were combined and concentrated by rotary evaporation to give 3.7 g (49%) of an analytically pure oil.

| Analysis: | |
|---|---|
| Calculated for $C_{31}H_{32}N_4OF_2$: | C, 72.35; H, 6.27; N, 10.89 |
| Found: | C, 72.32; H, 6.27; N, 10.83 |

TABLE 1

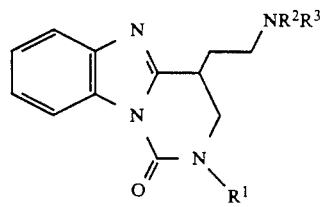

| Example | $R^1$ | $NR^2R^3$ | Salt |
|---|---|---|---|
| 1 | —$CH_3$ | —$N(CH_3)_2$ | maleate.0.5 $H_2O$ |
| 2 | —$CH_3$ | —N(morpholine) | — |
| 3 | —$CH_3$ | —N($C_6H_5$)($CH_3$) | — |
| 4 | —$CH_3$ | —N(piperazinyl)N—$CH_3$ | — |
| 5 | —$CH_3$ | —N(piperidinyl with $C_6H_5$, OH) | 1.5 Fumarate |
| 6 | —$CH_3$ | —N(piperazinyl)N—$C_6H_5$ | — |

TABLE 1-continued

[Structure: benzimidazole fused with a six-membered ring containing N-R¹ and C=O, with a side chain -CH(CH₂NR²R³)-CH₂- attached]

| Example | R¹ | NR²R³ | Salt |
|---------|----|----|------|
| 7 | —CH₃ | -N(piperazinyl)-2-pyridyl | — |
| 8 | —CH₃ | -N(piperazinyl)-2-pyrimidinyl | — |
| 9a | —C₂H₅ | —N(CH₃)₂ | — |
| 9b | —CH(CH₃)₂ | —N(CH₃)₂ | — |
| 9c | —(CH₂)₂CH₃ | —N(CH₃)₂ | — |
| 9d | —(CH₂)₃CH₃ | —N(CH₃)₂ | — |
| 10a | —C₂H₅ | morpholino | — |
| 10b | —CH(CH₃)₂ | morpholino | — |
| 10c | —(CH₂)₂CH₂ | morpholino | — |
| 10d | —(CH₂)₃CH₃ | morpholino | — |
| 11a | —CH₂CH₃ | —N(C₆H₅)(CH₃) | — |
| 11b | —CH(CH₃)₂ | —N(C₆H₅)(CH₃) | — |
| 11c | —(CH₂)₂CH₃ | —N(C₆H₅)(CH₃) | — |
| 11d | —(CH₂)₃CH₃ | —N(C₆H₅)(CH₃) | — |
| 12a | —CH₂CH₃ | -N(piperazinyl)NCH₃ | — |

TABLE 1-continued
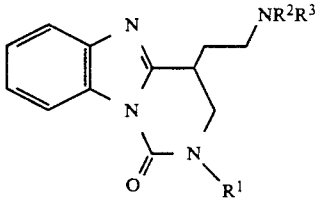
| Example | R¹ | NR²R³ | Salt |
|---|---|---|---|
| 12b | —CH(CH₃)₂ | 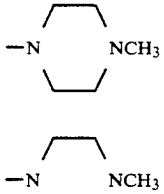 —N‾‾NCH₃ | — |
| 12c | —(CH₂)₂CH₃ | —N‾‾NCH₃ | — |
| 12d | —(CH₂)₃CH₃ | —N‾‾NCH₃ | — |
| 13a | —CH₂CH₃ | 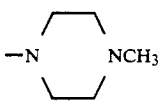 —N with C₆H₅, OH | — |
| 13b | —CH(CH₃)₂ | —N with C₆H₅, OH | — |
| 13c | —(CH₂)₂CH₃ | —N with C₆H₅, OH | — |
| 13d | —(CH₂)₃CH₃ | —N with C₆H₅, OH | — |
| 14a | —CH₂CH₃ | 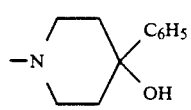 —N‾‾N—C₆H₅ | — |
| 14b | —CH(CH₃)₂ | —N‾‾N—C₆H₅ | — |
| 14c | —(CH₂)₂CH₃ | —N‾‾N—C₆H₅ | — |
| 14d | —(CH₂)₃CH₃ | —N‾‾N—C₆H₅ | — |

TABLE 1-continued

| Example | R¹ | NR²R³ | Salt |
|---|---|---|---|
| 15a | —CH₂CH₃ | piperazinyl-(2-pyridyl) | — |
| 15b | —CH(CH₃)₂ | piperazinyl-(2-pyridyl) | — |
| 15c | —(CH₂)₂CH₃ | piperazinyl-(2-pyridyl) | — |
| 15d | —(CH₂)₃CH₃ | piperazinyl-(2-pyridyl) | — |
| 16a | —CH₂CH₃ | piperazinyl-(2-pyrimidyl) | — |
| 16b | —CH(CH₃)₂ | piperazinyl-(2-pyrimidyl) | — |
| 16c | —(CH₂)₂CH₃ | piperazinyl-(2-pyrimidyl) | — |
| 16d | —(CH₂)₃CH₃ | piperazinyl-(2-pyrimidyl) | — |
| 17 | —CH₃ | 1-phenyl-1,3,8-triazaspiro[4.5]decan-4-on-8-yl | ethyl acetate |
| 18 | —CH₃ | 4-(2-methoxyphenyl)piperazin-1-yl | Fumarate |

TABLE 1-continued

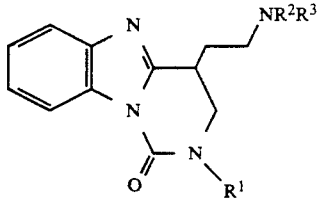

| Example | R¹ | NR²R³ | Salt |
|---------|-----|-------|------|
| 19 | —CH₃ | 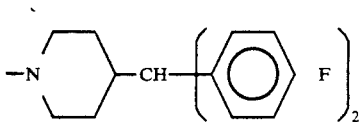 | Oxalate |
| 20 | —CH₃ | —N⟨piperidine⟩—CH—[(C₆H₄)F]₂ | — |

PHARMACOLOGY

Coronary Artery Ligation Induced Arrhythmias

Adult mongrel dogs which are in the conscious state are used for the test and cardiac arrhythmias are induced by prior (22-24 hr) surgical preparation in which blood flow through a coronary artery is occluded by use of a constrictor device as reported by Smith et al, 1973. A Grass Model 79 Polygraph is used for recording the electrocardiogram (Grass 7P4 Preamplifier).

The test compound in a suitable vehicle is administered by infusion (Harvard Model 942 Infusion Pump) into a saphenous vein to one group of dogs at a rate of 0.5 mg/kg/min. Concentration of compound is adjusted according to the weight of the dog to allow a volume of infusion of 0.5 ml/min. To determine oral efficacy the test compound is administered orally by gavage to another group of dogs at dose levels of 10 through 40 mg/kg. For oral dosing the test compound is prepared in distilled water to give a total volume of 20 ml. Following the administration of the test compound, the heart rate, number of ectopic cardiac beats per min, and the percent ectopic beats (ectopic beats/hr X100) are recorded at 15 min intervals. The compound is considered active if it abolishes the ectopic ventricular frequency and causes a return to normal sinus rhythm within 2 hours of administration. For example, the minimally effective dose for 100% reduction in ectopic ventricular beats was 3 mg/kg (IV) for the compounds of Examples 1 and 8.

Cardiac arrhythmias are produced by a modification of the method of Harris, 1950, *Circulation*, 1, 1318 as reported by Smith et al., 1973, *Pharmacologist* 15, 192.

Pharmaceutical Compositions

The invention further provides pharmaceutical compositions for administration to a living animal body comprising, as active ingredients, at least one of the compounds according to the invention in association with a pharmaceutical carrier or excipient. The compounds are thus presented in a therapeutic composition suitable for oral, rectal or parenteral administration. Thus, for example, compositions for oral administration are preferably solids and can take the form of capsules, tablets or coated tablets containing carriers conveniently used in the pharmaceutical art. Suitable tableting carriers or excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid, e.g., water, or a parenterally acceptable oil; e.g., arachis oil, contained in ampoules.

In compositions for rectal administration the carrier can comprise a suppository base, e.g., cocoa butter, or a glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable effective dosage will be obtained consistent with the dosage form employed. The exact individual dosages, as well as daily dosages, will, of course, be determined according to standard medical principles under the direction of a physician or veterinarian. Generally the oral effective dose to either prevent or treat cardiac arrhythmias as compared with disopyramide would consist of unit dosages containing an amount of compound equivalent to about 1 to about 10 mg/kg of body weight and thus are contemplated. Based on all of the above considerations, a choice in a range of unit oral dosages for humans of about 10 to about 1000 mg is contemplated, preferably about 10 to 600 mg. Daily dosages of about 100 to 1200 mg are contemplated for humans and obviously several unit dosage forms may be administered at about the same time. However, the scope of the invention is not to be limited by these contemplations due to the uncertainty in transpositions discussed above.

Examples of unit dosage compositions are as follows:

| Capsules | |
|----------|---|
| Ingredients | Per Cap. |
| 1. Active ingredient | 75.0 mg |
| 2. Lactose | 146.0 mg |
| 3. Magnesium Stearate | 4.0 mg |

| Capsules | |
|---|---|
| Ingredients | Per Cap. |
| | 219.0 mg |

Procedure

Step 1. Blend ingredients 1, 2 and 3.
Step 2. Pass blend from Step 1 through a No. 30 mesh screen (0.59 mm) and blend again.
Step 3. Fill powder blend from Step 2 into No. 1 hard gelatin capsules.

| Ingredients | Mg./Tab. |
|---|---|
| Tablets (50 mg) | |
| 1. Active Ingredient | 50.0 mg |
| 2. Corn starch | 20.0 mg |
| 3. Alginic acid | 20.0 mg |
| 4. Sodium alginate | 20.0 mg |
| 5. Magnesium stearate | 1.3 mg |
| | 111.3 mg |
| Tablets (75 mg) | |
| 1. Active ingredient | 75.0 mg |
| 2. Milo starch | 20.0 mg |
| 3. Corn starch | 38.0 mg |
| 4. Lactose | 90.0 mg |
| 5. Magnesium stearate | 2.0 mg |
| | 225.0 mg |

Procedure

Step 1. Blend ingredients 1, 2 and 3 and 4.
Step 2. Add sufficient water portion wise to the blend from Step 1 with careful stirring after each addition. Such additions of water and stirring continue until the mass is of a consistency to permit its conversion to wet granules.
Step 3. The wet mass prepared in Step 2 is converted to granules by passing it through an oscillating granulator, using a #8-mesh (2.36 mm) screen.
Step 4. The wet granules prepared in Step 3 are dried in an oven at 140° F.
Step 5. Dried granules from Step 4 are passed through an oscillating granulator, using a No. 10-mesh (2.00 mm) screen.
Step 6. Lubricate the dry granules from Step 5 by blending with ingredient No. 5.
Step 7. The lubricated granules from Step 6 are compressed on a suitable tablet press.

| Intravenous Injection | |
|---|---|
| Ingredients | Per ml. |
| 1. Active Ingredient | 10.0 mg |
| 2. Isotonic pH 4.0 buffer solution q.s. to | 1.0 ml |

Procedure

Step 1. Dissolve the active ingredient in the buffer solution.
Step 2. Aseptically filter the solution from Step 1.
Step 3. The sterile solution is now aseptically filled into sterile ampouls.
Step 4. The ampouls are sealed under aseptic conditions.

| Intramuscular Injection | |
|---|---|
| Ingredients | Per ml. |
| 1. Active ingredients | 50.0 mg |
| 2. Isotonic pH 4.0 buffer solution q.s. to | 5.0 ml |

Procedure

Step 1. Dissolve the active ingredient in the buffer solution.
Step 2. Aseptically filter the solution from Step 1.
Step 3. The sterile solution is now aseptically filled into sterile ampouls.
Step 4. The ampouls are sealed under aseptic conditions.

| Suppositories | |
|---|---|
| Ingredients | Per Supp. |
| 1. Active ingredient | 200.0 mg |
| 2. Polyethylene Glycol 1000 | 1350.0 mg |
| 3. Polyethylene Glycol 4000 | 450.0 mg |
| | 2000.0 mg |

Procedure

Step 1. Melt ingredients 2 and 3 together and stir until uniform.
Step 2. Dissolve 1 in the molten mass from Step 1 and stir until uniform.
Step 3. Pour the molten mass from Step 2 into suppository molds and allow to cool.
Step 4. Remove the suppositories from molds and wrap.

Various modifications and equivalents will be apparent to one skilled in the art and may be made in the compounds, method, and compositions of the present invention without departing from the spirit or scope thereof, and it is therefore to be understood that the invention is to be limited only the scope of the appended claims.

What is claimed is:

1. An antiarrhythmic compound having the formula:

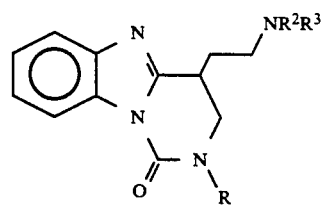

where $R^1$ is loweralkyl;
$R^2$ and $R^3$ are independently selected from H, loweralkyl, phenyl or phenyl substituted by 1 or 2 substituents selected from the group consisting of halogen, hydroxy, loweralkoxy, or loweralkylcarbonyl or —$NR^2R^3$ forms a heterocyclic group selected from the group consisting of imidazole, morpholine,

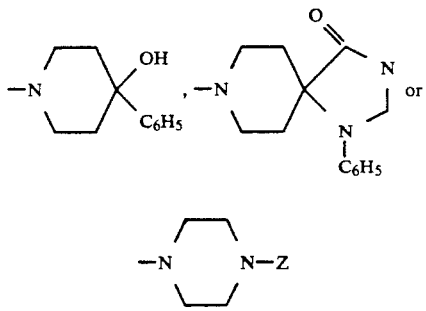

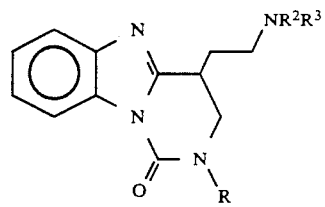

where Z is loweralkyl, phenyl or phenyl substituted by 1 or 2 substituents selected from the group consisting of halogen, hydroxy, loweralkoxy, or loweralkylcarbonyl, 2-pyridinyl or 2-pyrimidinyl; an optical isomer or a pharmaceutically acceptable salt thereof.

2. A compound of claim 1, which is 4-[2-(dimethylamino)ethyl]-3,4-dihydro-2-methylpyrimido[1,6-a]benzimidazol-1(2H)-one or a pharmaceutically acceptable salt thereof.

3. A compound of claim 1, which is 3,4-dihydro-2-methyl-4-[2-(4-morpholinyl)ethyl]pyrimido[1,6-a]benzimidazol-1(2H)-one or a pharmaceutically acceptable salt thereof.

4. A compound of claim 1, which is 3,4-dihydro-2-methyl-4-[2-(methylphenylamino)ethyl]pyrimdo[1,6-a]benzimidaol-1(2H)-one or a pharmaceutically acceptable salt thereof.

5. A compound of claim 1, which is 3,4-dihydro-2-methyl-4-[2-(4-methyl-1-piperazinyl)ethyl]-pyrimido[1,6-a]benzimidazol-1(2H)-one or a pharmaceutically acceptable salt thereof.

6. A compound of claim 1, which is 3,4-dihydro-4-[2-(4-hydroxy-4-phenyl-1-piperidinyl)ethyl]-2-methyl-pyrimido[1,6-a]benzimidazol-1(2H)-one or a pharmaceutically acceptable salt thereof.

7. A compound of claim 1, which is 3,4-dihydro-2-methyl-4-[2-(4-phenyl-1-piperazinyl)ethyl]-pyrimido[1,6-a]benzimidazol-1(2H)-one or a pharmaceutically acceptable salt thereof.

8. A compound of claim 1, which is 3,4-dihydro-2-methyl-4-[2-[4-(2-pyridinyl)-1-piperazinyl]ethyl]-pyrimido[1,6-a]benzimidazol-1(2H)-one or a pharmaceutically acceptable salt thereof.

9. A compound of claim 1, which is 3,4-dihydro-2-methyl-4-[2-[4-(2-pyrimidinyl)-1-piperazinyl]ethyl]-pyrimido[1,6-a]benzimidazol-1(2H)-one or a pharmaceutically acceptable salt thereof.

10. A compound of claim 1, which is 3,4-dihydro-2-methyl-4-[2-(4-oxo-1-phenyl-1,3,8-triazaspiro[4,5]dec-8-yl)ethyl]pyrimido[1,6-a]benzimidazol-1(2H)-one or a pharmaceutically acceptable salt thereof.

11. A compound of claim 1, which is 3,4-dihydro-4-[2-[4-(2-methoxyphenyl)-1-piperazinyl]ethyl]-2-methylpyrimido[1,6-a]benzimidazol-1(2H)-one or a pharmaceutically acceptable salt thereof.

12. A compound of claim 1, which is 3,4-dihydro-2-methyl-4-[2-(1H-imidazol-1-yl)ethyl]pyrimido[1,6-a]benzimidazol-1(2H)-one or a pharmaceutically acceptable salt thereof.

13. A compound of claim 1, which is 4-[2-[bis(4-fluorophenyl)methyl-1-piperidinyl]ethyl]3,4-dihydro-2-methylpyrimido[1,6-a]benzimidazol-1(2H)-one or a pharmaceutically acceptable salt thereof.

14. A method for treating cardiac arrhythmias in a warm blooded animal which comprises administering thereto a therapeutically effective amount for treating cardiac arrhythmias of a compound having the formula:

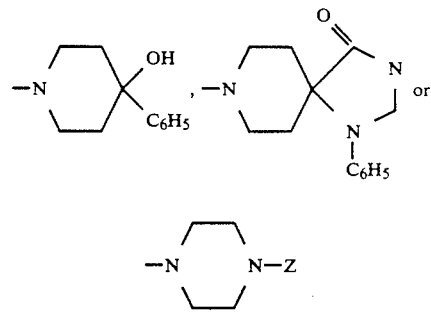

where $R^1$ is loweralkyl;
$R^2$ and $R^3$ are independently selected from H, loweralkyl, phenyl or phenyl substituted by 1 or 2 substituents selected from the group consisting of halogen, hydroxy, loweralkoxy, or loweralkylcarbonyl or —$NR^2R^3$ forms a heterocyclic group selected from the group consisting of imidazole, morpholine,

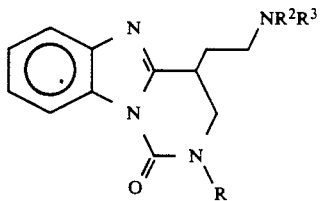

where Z is loweralkyl, phenyl or phenyl substituted by 1 or 2 substituents selected from the group consisting of halogen, hydroxy, loweralkoxy, or loweralkylcarbonyl, 2-pyridinyl or 2-pyrimidinyl; an optical isomer or a pharmaceutically acceptable salt thereof.

15. A pharmaceutical composition useful in treating cardiac arrhythmias which is comprised of:
a. a therapeutically effective amount for treating cardiac arrhythmias of a compound having the formula:

where $R^1$ is loweralkyl;
$R^2$ and $R^3$ are inependently selected from H, loweralkyl, phenyl or phenyl substituted by 1 or 2 substituents selected from the group consisting of halogen, hydroxy, loweralkoxy, or loweralkylcarbonyl or —$NR^2R^3$ forms a heterocyclic group selected from the group consisting of imidazole, morpholine,

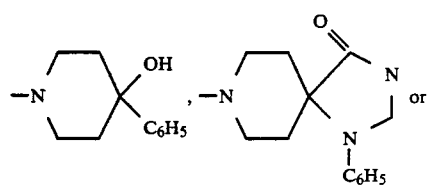 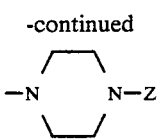
where Z is loweralkyl, phenyl or phenyl substituted by 1 or 2 substituents selected from the group consisting of halogen, hydroxy, loweralkoxy, or loweralkylcarbonyl, 2-pyridinyl or 2-pyrimidinyl; an optical isomer or a pharmaceutically acceptable salt thereof, and;
b. a pharmaceutical carrier.
* * * * *